US010184127B2

(12) United States Patent
van Sinderen et al.

(10) Patent No.: US 10,184,127 B2
(45) Date of Patent: Jan. 22, 2019

(54) GENETIC TRANSFORMATION OF BIFIDOBACTERIA

(71) Applicants: Compagnie Gervais Danone, Paris (FR); University College Cork—National University of Ireland, Cork, Cork (IE)

(72) Inventors: Douwe van Sinderen, Carriggrohane (IE); Mary O'Connell Motherway, Ladysbridge (IE); Debbie Watson, Mallow (IE); Tamara Smokvina, Orsay (FR); Peggy Garault, Montlhery (FR)

(73) Assignees: Compagnie Gervais Danone, Paris (FR); University College Cork—National University of Ireland, Cork, Cork (IE)

( * ) Notice: Subject to any disclaimer, the term of this patent is extended or adjusted under 35 U.S.C. 154(b) by 4 days.

(21) Appl. No.: 15/101,078

(22) PCT Filed: Dec. 2, 2013

(86) PCT No.: PCT/IB2013/002951
§ 371 (c)(1),
(2) Date: Jun. 2, 2016

(87) PCT Pub. No.: WO2015/082949
PCT Pub. Date: Jun. 11, 2015

(65) Prior Publication Data
US 2016/0304885 A1    Oct. 20, 2016

(51) Int. Cl.
| | |
|---|---|
| C12P 21/06 | (2006.01) |
| A61K 39/00 | (2006.01) |
| A61K 39/38 | (2006.01) |
| C12N 15/74 | (2006.01) |
| C12N 1/20 | (2006.01) |
| C12N 9/10 | (2006.01) |

(52) U.S. Cl.
CPC ............ *C12N 15/746* (2013.01); *C12N 1/20* (2013.01); *C12N 9/1007* (2013.01); *C12Y 201/01* (2013.01)

(58) Field of Classification Search
CPC ...... A61K 39/02; A61K 39/0258; C12N 1/00; C12N 1/20
USPC ........... 424/184.1, 185.1, 190.1, 200.1, 93.1, 424/93.2, 234.1, 241.1; 435/41, 69.1, 435/71.1
See application file for complete search history.

(56) References Cited

PUBLICATIONS

International Search Report issued in corresponding International Patent Application No. PCT/IB2013/002951 dated Jan. 7, 2015.
Kim et al., "Genome Sequence of the Probiotic Bacterium *Bifidobacterium animalis* subsp. *lactis* AD011," Journal of Bacteriology, 191: 678-679 (2009).
Chervaux et al., "Genome Sequence of the Probiotic Strain *Bifidovacterium animalis* subsp. *lactis* CNCM I-2494," Journal of Bacteriology, 193: 5560-5561 (2011).
Stahl et al., "Complete Genome Sequences of Probiotic Strains *Bifidobacterium animalis* subsp. *lactis* B420 and Bi-07," Journal of Bacteriology, 194: 4131-4132 (2012).
Brancaccio et al., "Tough nuts to crack: Site-directed mutagenesis of bifidobacteria remains a challenge," Bioengineered, 4: 197-202 (2013).
O'Connell Motherway et al., "Overcoming the restriction barrier to plasmid transformation and targeted mutagenesis in Bifidobacterium breve UCC2003," Microbial Biotechnology, 2: 321-332 (2009).
Yasui et al., "Improvement of bacterial transformation efficiency using plasmid artificial modification," Nucleic Acids Research, 37: E3 (2008).
Cronin et al., "Progress in genomics, metabolism and biotechnology of bifidobacteria," International Journal of Food Microbiology, 149: 4-18 (2011).
Guglielmetti et al., "Mobilome and genetic modification of bifidobacteria," Beneficial Microbes, 4: 143-166 (2013).
Masco et al., "Polyphasic taxonomic analysis of Bifidobacterium animalis and Bifidobacterium lactis reveals relatedness at the subspecies level: reclassification of Bifidobacterium animalis as *Bifidobacterium animalis* subsp. *animalis* subsp. nov. and Bifidobacterium lactis as *Bifidobacterium animalis* subsp. *lactis* subsp. nov.," International Journal of Systematic and Evolutionary Microbiology, 54: 1137-1143 (2004).
Ruas-Madiedo et al., "A Bile Salt-Resistant Derivative of Bifidobacterium animalis Has an Altered Fermentation Pattern When Grown on Glucose and Maltose," Applied and Environmental Microbiology, 71: 6564-6570 (2005).
O'Connell Motherway et al., "Identification of Restriction-Modification Systems of *Bifidobacterium animalis* subsp. *lactis* CNCM I-2494 by SMRT Sequencing and Associated Methylome Analysis," PLOS One, 9: e94875 (2014).
Charteris et al., "Edible table (bio)spread containing potentially probiotic *Lactobacillus* and *Bifidobacterium* species," International Journal of Dairy Technology, Society of Dairy Technology, 55: 44-56 (2002).
Dave et al., "Evaluation of Media for Selective Enumeration of *Streptococcus thermophilus, Lactobacillus delbrueckii* ssp. *bulgaricus*, Lactobacillus acidophilus, and Bifidobacteria," Journal of Dairy Science, 79: 1529-1536 (1996).
Rybka et al., "Short Communication: Media for the Enumeration of Yoghurt Bacteria," International Dairy Journal, 6: 839-850 (1996).
Endo et al., "*Bifidobacterium reuteri* sp. nov., *Bifidobacterium callitrichos* sp. nov., *Bifidobacterium saguini* sp. nov., *Bifidobacterium stellenboschense* sp. nov. and *Bifidobacterium biavatii* sp. nov. isolated from faeces of common marmoset (*Callithrix jacchus*) and red-handed tamarin (*Saguinus midas*)," Systematic and Applied Microbiology, 35: 92-97 (2012).

(Continued)

*Primary Examiner* — Rodney P Swartz
(74) *Attorney, Agent, or Firm* — Morgan, Lewis & Bockius LLP

(57) ABSTRACT

The present invention concerns a method for genetically transforming a *Bifidobacterium* strain comprising a step of methylation of a shuttle vector in an *E. coli* or a Gram-positive bacterium strain by two type II DNA methyltransferases from a *Bifidobacterium*: a methyltransferase enzyme that methylates the adenine base at position 4 of the nucleotide sequence RTCAGG and a methyltransferase enzyme that methylates the cytosine base at position 4 of the nucleotide sequence GGWCC. The present invention also concerns genetic tools and culture media useful for carrying out said method.

9 Claims, 7 Drawing Sheets
Specification includes a Sequence Listing.

(56) References Cited

PUBLICATIONS

Tabasco et al., "Selective enumeration and identification of mixed cultures of *Streptococcus thermophilus, Lactobacillus delbrueckii* subsp. *bulgaricus, L. acidophilus, L. paracasei* subsp. paracasei and Bifidobacterium lactis in fermented milk," International Dairy Journal, 17: 1107-1114 (2007).
Uniprot, ID: B8DWT7_BIFA0 (2009).
Uniprot, ID: G0H814_BIFAN (2011).
Uniprot, ID: I6PVJ3_BIFAN (2012).

SEQUENCE LISTING

<160> NUMBER OF SEQ ID NOS: 15

<210> SEQ ID NO 1
<211> LENGTH: 363
<212> TYPE: PRT
<213> ORGANISM: Bifidobacterium lactis

<400> SEQUENCE: 1

Met Ala Thr Pro Leu Asn Arg Ala Asn Gln Ala Lys Glu Asp Glu Phe
1               5                   10                  15

Tyr Thr Gln Leu Ser Asp Ile Glu Ser Glu Leu Lys His Tyr Arg Lys
            20                  25                  30

His Phe Ala Gly Lys Thr Val Leu Cys Asn Cys Asp Asp Pro Phe Glu
        35                  40                  45

Ser Asn Phe Phe Lys Tyr Phe Cys Leu Asn Phe Asn Arg Leu Lys Leu
    50                  55                  60

Lys Lys Leu Ile Ala Thr Cys Tyr Ser Gly Ser Pro Ile Thr Gly Asn
65                  70                  75                  80

Glu Leu Thr Leu Phe Gly Asp Asp Thr Glu Glu Arg Arg Thr Pro
                85                  90                  95

Tyr Lys Ala Val Val Thr Ser Val Arg Asp Ala Asn Gly Asp Gly Ala
            100                 105                 110

Thr Ser Met Val Asp Val Ala Glu Leu Phe Lys Gln Gly Glu Asn Leu
        115                 120                 125

Cys Glu Arg Leu Glu Gly Asn Gly Asp Phe Arg Ser Glu Glu Cys Leu
    130                 135                 140

Arg Leu Leu Asp Glu Ala Asp Ile Val Val Thr Asn Pro Pro Phe Ser
145                 150                 155                 160

Lys Phe Arg Glu Phe Val Ser Thr Leu Val Glu His Asp Lys Lys Phe
                165                 170                 175

Ile Ile Ile Gly Asn Gln Asn Ala Ile Thr Tyr Lys Glu Phe Phe Pro
            180                 185                 190

Leu Leu Arg Asp Asn Lys Val Trp Leu Gly Tyr Gly Cys Gly Asp Met
        195                 200                 205

Ala Phe Lys Val Pro Asp Asp Tyr Glu Pro Arg Lys Thr Arg Tyr Trp
    210                 215                 220

Gln Asp Glu Ser Gly Gln Lys Trp Arg Ser Met Gly Asn Ala Cys Trp
225                 230                 235                 240

```
Tyr Thr Asn Leu Asp Ile Lys Lys Arg His Glu Asp Leu Val Leu Val
            245                 250                 255

Lys Arg Tyr Asn Arg Asp Asp Tyr Pro Lys Tyr Asp Asn Tyr Glu Ala
            260                 265                 270

Ile Asn Val Gly Lys Val Ile Asp Ile Pro Cys Asp Tyr Glu Gly Ile
            275                 280             285

Met Gly Val Pro Val Thr Phe Met Asp Lys Phe Asn Pro Asp Gln Phe
290                     295                 300

Glu Ile Ile Gly Leu Leu Ala Gly Asn Ile Arg Gly Leu Ala Gly Ile
305                 310                 315                 320

Pro Ser Ser Thr Gly Lys Asp Gly Pro Tyr Ile Asn Gly Lys Leu Lys
            325                 330                 335

Phe Gly Arg Ile Leu Val Arg Asn Leu His Pro Glu Pro Arg Pro Tyr
            340                 345                 350

Glu Thr Val Thr Leu Glu Glu Ala Gln Gly Lys
            355                 360
```

<210> SEQ ID NO 2
<211> LENGTH: 1092
<212> TYPE: DNA
<213> ORGANISM: Bifidobacterium lactis

<400> SEQUENCE: 2

```
atggctacgc ctctcaatcg agcaaatcag gcgaaagaag acgagttcta cactcagttg      60
tcagacatcg aatctgagtt gaaacattat cggaagcatt ttgcgggcaa gacggtgttg     120
tgcaattgtg atgatccatt cgaatctaat ttcttcaaat atttctgctt aaatttcaat     180
cgtctgaagt tgaagaagct cattgcaact tgctattcag gatccccgat aacagggaac     240
gagctcacgc ttttcggtga cgacacagaa gaggaaaggc gcacgcctta caaggctgtt     300
gtgacttctg tgcgtgatgc caatggtgat ggtgctacca gcatggttga cgtggccgaa     360
ttgttcaagc agggcgagaa ccctttgcga acgtctagaa gcaacggcga tttcagatca     420
gaagaatgcc tgagattgct agatgaagcg gacatcgtgg tgaccaatcc gcctttctcg     480
aaattccgtg aattcgtgtc taccctttgtg gagcatgata agaaattcat catcatcggt     540
aaccaaaacg ctatcaccta taggagttc ttccccctat tgcgggataa caaagtctgg     600
ctgggctatg gttgtggcga tatggcgttt aaggttccag atgactatga gccgcgtaaa     660
acgcgatatt ggcaagatga gagcgggcag aagtggcgat ccatgggaaa tgcctgttgg     720
tacaccaatc tcgacatcaa gaagcgccat gaagacctag ttctggttaa gcgttacaat     780
cgcgacgatt acccaaagta tgacaattac gaagccatca atgtcggtaa ggtgattgat     840
attccttgtg attatgaggg aatcatgggt gtacccgtca cattcatgga caagttcaat     900
ccggatcagt tcgagattat cgggctactt gctggcaata tccggggatt agccggcatt     960
ccgtcctcta ctggtaagga cggcccatac atcaacggca agctgaaatt cgggcggata    1020
cttgtccgca acttgcaccc cgaacctcgc ccctatgaaa cagtcactct cgaagaagcg    1080
caaggaaagt aa                                                        1092
```

<210> SEQ ID NO 3
<211> LENGTH: 502
<212> TYPE: PRT
<213> ORGANISM: Bifidobacterium lactis

```
<400> SEQUENCE: 3

Met Pro Arg Val Phe Asn Cys Glu Leu Ser Leu Glu His Gly Val Arg
1               5                  10                  15

Arg Asp Cys Ala Ile Val Leu Ala Ser Lys Val Leu Val Tyr Gly
            20                  25                  30

Ile Thr Glu Ser Thr His Phe Val Pro Val Lys Leu Tyr Asp Trp
        35                  40                  45

Gly Met Ser Glu Asn Ala Leu Leu Asn Thr Lys Glu Thr Ala Gln Tyr
    50                  55                  60

Ile Gly Val Ser Ala Gly Val Val Thr Arg Leu Ala Asn Thr Gly Glu
65                  70                  75                  80

Leu Glu Phe Asp Thr Cys Gly Ala Arg Lys Val Phe Arg Lys Glu Ala
                85                  90                  95

Ile Asp Ala Tyr Leu Glu Arg Asn Asn Leu Ile Gln Ala Ala Val Asp
            100                 105                 110

Gln Val Ser Thr Lys Asp Phe Glu Asp Asn Ile Cys Ala Leu Ser Phe
        115                 120                 125

Phe Ser Gly Ala Gly Gly Leu Asp Leu Gly Phe Glu Arg Ala Gly Ile
    130                 135                 140

Ser Ala Ala Leu Tyr Cys Glu Asn Asn Arg Glu Cys Arg Met Thr Leu
145                 150                 155                 160

His Arg Asn Arg Pro Asp Val Ala Leu Leu Gly Asp Ile Thr Lys Ile
                165                 170                 175

Ser Ala Asp Glu Val Arg Arg Met Ala Arg Ile Pro Gln Gly Arg Glu
            180                 185                 190

Ile Asp Val Met Phe Gly Gly Pro Pro Cys Gln Ala Phe Ser Thr Ala
        195                 200                 205

Gly Ala Arg Arg Ala Phe Glu Asp Pro Arg Gly Asn Val Phe Leu Arg
    210                 215                 220

Tyr Leu Asp Leu Ala Ser Glu Leu Lys Pro Arg Tyr Leu Val Ile Glu
225                 230                 235                 240

Asn Val Arg Gly Leu Leu Ser Thr Pro Phe Pro Val Glu Ser Gly Gly
                245                 250                 255

Lys Pro Ile Arg Gly Gly Val Met Arg Tyr Ile Leu Asn Lys Leu Glu
            260                 265                 270

Glu Met Gly Tyr Gly Val Ser Phe Asn Leu Tyr Asn Ala Ala Asn Phe
        275                 280                 285

Gly Ala Ala Gln Ile Arg Glu Arg Val Val Ile Ala Lys Arg Asp
    290                 295                 300

Gly Thr Lys Cys Asp Trp Leu Ile Pro Thr His Thr Asp Pro Asp Gly
305                 310                 315                 320

Lys Tyr Val Gln Asn Trp Asn Leu Pro Ser Trp Val Thr Phe Arg Asp
                325                 330                 335

Val Val Tyr Asp Ile Glu Asp Ser Arg Gln Thr His Thr Asp Phe Pro
            340                 345                 350

Glu Lys Arg Leu Leu Tyr Phe Ser Met Leu Lys Glu Gly Gln Cys Trp
        355                 360                 365

Asn Lys Leu Pro Ile Glu Ile Gln Glu Glu Ala Met Gly Lys Ala Tyr
    370                 375                 380

Lys Leu Gly Gly Gly Lys Thr Gly Phe Tyr Arg Arg Ile Ala Trp Asp
385                 390                 395                 400

Arg Pro Ser Pro Thr Leu Val Thr Ser Pro Thr Met Pro Ala Thr Asp
                405                 410                 415
```

```
Leu Cys His Pro Lys Glu Leu Arg Pro Leu Ser Val Glu Glu Tyr Lys
            420                 425                 430

Arg Val Gln Gly Phe Pro Asp Asp Trp Trp Ile Ala Gly Ser Ile His
            435                 440                 445

Asp Gln Tyr Arg Gln Ile Gly Asn Ala Val Pro Val Ser Leu Gly Glu
        450                 455                 460

Ala Ile Gly Arg Ala Ile Leu Asp Asp Met Arg Gly Glu Ala His Asp
465                 470                 475                 480

Glu Arg Trp Arg Asn Phe Pro Tyr Ser Arg Tyr Ala His Thr Ser Asp
                485                 490                 495

Gln Asn Trp Asn Leu Ala
            500

<210> SEQ ID NO 4
<211> LENGTH: 1509
<212> TYPE: DNA
<213> ORGANISM: Bifidobacterium lactis

<400> SEQUENCE: 4
atgccgcgtg tgttcaattg tgagttgagt ctcgagcatg gtgtgagacg ggattgcgct      60
attgttctcg cctccaaggt tctagtggta tatggaatca ccgaaagtac tcattttgta     120
gtccctgtta aactatatga ttggggtatg tcggaaaacg cgctgctgaa cactaaggaa     180
acagcccaat atatagggt gtctgcgggt gtagtgacac gtctcgcgaa tacgggcgaa     240
cttgagtttg acacctgcgg agctcgtaaa gttttccgta agaagccat cgacgcatat     300
ctggaacgga ataatctgat tcaagctgcg gtggatcaag tgtcaactaa agacttcgag     360
gacaacatct gcgctctctc attttttcagt ggggctggcg gtctggatct tggctttgag     420
cgagctggca tatcggcggc actatattgt gagaacaatc gtgaatgccg tatgaccttg     480
catcgaaacc gtccagatgt cgccctgctc ggagatatca ccaaaatcag tgccgacgag     540
gttcgtcgaa tggcccgtat ccctcagggg cgtgaaatcg atgtgatgtt cggcggtccg     600
ccatgccaag cattttcaac agcaggcgcg cgccgtgcat tcgaggatcc ccgcggcaat     660
gtatttctca gatacttgga cttggcctcc gaattgaagc gcgatacct agtcatagaa     720
aacgtacgcg gactgctctc caccccttt cccgttgaat ctggcgggaa gccaatccgg     780
ggcggagtga tgcgctacat actcaataag ttggaagaga tgggctacgg tgtttcgttc     840
aatctctaca cgcggctaa cttggagcg gcccagattc gtgagcgtgt ggtcattatt     900
gccaaacgtg atggcacgaa gtgtgactgg ctcataccta cgcatactga tcctgatggc     960
aaatatgtcc aaaactggaa tcttccctct tgggtaacgt tccgagacgt tgtctacgat    1020
attgaagatt ctcggcaaac ccacactgat ttccctgaga gcggttgct ttacttcagc    1080
atgctgaaag aggggcagtg ctggaacaaa ctccccatcg aaattcaaga ggaggctatg    1140
ggtaaggcct ataagcttgg aggcggcaag accggattct accgacgcat cgcttgggat    1200
agaccatccc ccactctggt caccagccca acgatgccag ccaccgacct tgccatccc     1260
aaggagctgc gaccgctgag cgtggaagaa tataaacggg tgcagggttt ccctgatgat    1320
tggtggattg ctggcagcat tcacgaccag taccgccaaa tcggcaacgc cgttccggtc    1380
agcttgggcg aagcaattgg ccgagcaatt ctcgatgaca tgaggggaga ggctcatgat    1440
gagcgttggc gcaattttccc ctattcaaga tatgcccata ccagcgatca aaactggaat    1500
ctggcctga                                                           1509
```

<210> SEQ ID NO 5
<211> LENGTH: 51
<212> TYPE: DNA
<213> ORGANISM: Artificial Sequence
<220> FEATURE:
<223> OTHER INFORMATION: Primer

<400> SEQUENCE: 5
cgtccgctgc agataaggag gcactcacca tggctacgcc tctcaatcga g        51

<210> SEQ ID NO 6
<211> LENGTH: 34
<212> TYPE: DNA
<213> ORGANISM: Artificial Sequence
<220> FEATURE:
<223> OTHER INFORMATION: Primer

<400> SEQUENCE: 6
gctctataag cttttacttt ccttgcgctt cttc        34

<210> SEQ ID NO 7
<211> LENGTH: 41
<212> TYPE: DNA
<213> ORGANISM: Artificial Sequence
<220> FEATURE:
<223> OTHER INFORMATION: Primer

<400> SEQUENCE: 7
cgtccgagat ctgttagttg aagaaggttt ttatattaca g        41

<210> SEQ ID NO 8
<211> LENGTH: 49
<212> TYPE: DNA
<213> ORGANISM: Artificial Sequence
<220> FEATURE:
<223> OTHER INFORMATION: Primer

<400> SEQUENCE: 8
cgtccgtcta gaataaggag gcactcacca tgccgcgtgt gttcaattg        49

<210> SEQ ID NO 9
<211> LENGTH: 31
<212> TYPE: DNA
<213> ORGANISM: Artificial Sequence
<220> FEATURE:
<223> OTHER INFORMATION: Primer

<400> SEQUENCE: 9
gctctactgc agcaatggag gcgtgcaaat c        31

<210> SEQ ID NO 10
<211> LENGTH: 34
<212> TYPE: DNA
<213> ORGANISM: Artificial Sequence
<220> FEATURE:
<223> OTHER INFORMATION: Primer

<400> SEQUENCE: 10
tcagctgtcg acacaattgt aacccataca ggag        34

<210> SEQ ID NO 11
<211> LENGTH: 34
<212> TYPE: DNA
<213> ORGANISM: Artificial Sequence
<220> FEATURE:
<223> OTHER INFORMATION: Primer

```
<400> SEQUENCE: 11
gcgacggtcg actttacttt ccttgcgctt cttc                                    34

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12
gtcctggagc tcgcacacga aaacaagtt aag                                      33

<210> SEQ ID NO 13
<211> LENGTH: 39
<212> TYPE: DNA
<213> ORGANISM: Artificial Sequence
<220> FEATURE:
<223> OTHER INFORMATION: Primer

<400> SEQUENCE: 13
ctggaagagc tccaatgaat aggtttacac ttactttag                               39

<210> SEQ ID NO 14
<211> LENGTH: 39
<212> TYPE: DNA
<213> ORGANISM: Artificial Sequence
<220> FEATURE:
<223> OTHER INFORMATION: Primer

<400> SEQUENCE: 14
ctggaaaagc ttcaatgaat aggtttacac ttactttag                               39

<210> SEQ ID NO 15
<211> LENGTH: 33
<212> TYPE: DNA
<213> ORGANISM: Artificial Sequence
<220> FEATURE:
<223> OTHER INFORMATION: Primer

<400> SEQUENCE: 15
gtcctggaat tcgcacacga aaacaagtt aag                                      33
```

GENETIC TRANSFORMATION OF BIFIDOBACTERIA

SEQUENCE LISTING SUBMISSION VIA EFS-WEB

A computer readable text file, entitled "SequenceListing.txt," created on or about May 26, 2016 with a file size of about 14 kb contains the sequence listing for this application and is hereby incorporated by reference in its entirety.

The present invention relates to methods and means for genetically transforming a *Bifidobacterium* strain.

Bifidobacteria are Gram-positive bacteria. They are mainly found in the gastrointestinal tract of mammals, in particular humans. Species of the genus *Bifidobacterium* have increased industrial potential because of their health-associated benefits. They are widely used as probiotic organisms in a vast array of compositions for preventing or treating many intestinal disorders. Certain members of the *Bifidobacterium* genus are used for the preparation of fermented milk products. By way of example, *Bifidobacterium animalis* subsp. *lactis* CNCM 1-2494 deposited according to the Budapest Treaty with the CNCM on Jun. 20, 2000 (also known under the code DN-173 010 and first disclosed in International Application WO 02/02800) was described as a glycosylation modulator of the gastro-intestinal cell surface.

While there is clinical evidence for the purported beneficial effects on health, there is still a lack of fundamental knowledge of the genetics of bifidobacteria and the molecular mechanisms by which they exert their beneficial activities. This is mainly because bifidobacteria are fastidious to grow since they require a rich media and mostly strict anaerobic conditions. Furthermore, they are considered to be recalcitrant to genetic transformation and currently just a few genetic engineering techniques are available to study them at the molecular level.

Several authors have reported on the development of vector systems to enhance transformation efficiency of bifidobacteria. However, low transformation efficiency still remains a major drawback using these strategies:

Missich R. et al. (1994, Plasmid. 32:208-11) reported on the construction of an *Escherichia coli-Bifidobacterium longum* (*B. longum*) shuttle vector, namely pRM2, and its transformation into *B. longum* by electroporation. However, Missich R. et al. point out a low transformation efficiency.

Argnani A. et al. (1996, Microbiology. 142:109-14) described the development of a transformation procedure for *Bifidobacterium* strains. Transformation was achieved using a plasmid, designated pDG7, that harbors bifidobacterial replication functions, and also with plasmids that bear replication functions from Corynebacteria. The transformation protocol is based on electroporation of bifidobacteria, which were made competent by pre-incubation in electroporation buffer for several hours at 4° C. Plasmids harboring replication functions originating from *Lactobacillus* species or *Lactococcus* strains frequently fail in their ability to transform bifidobacterial strains.

Rossi M. et al. (1996, Res Microbiol. 147:133-43) reported on the nucleotide sequence and characterization of the *B. longum* B2577 cryptic plasmid pMB1. Using the pMB1 replicon, a set of *E. coli*-bifidobacterial shuttle vectors was constructed and their ability to be transformed into *B. animalis* MB209 was evaluated.

Matsumura H. et al. (1997, Biosci Biotechnol Biochem. 61:1211-2) described the construction of an *E. coli*-bifidobacterial shuttle vector, namely pBLES 1000, and the transformation by electroporation of this vector into some, but not all, *B. longum* strains.

Guglielmetti S. et al. (2007, Appl Microbiol Biotechnol. 74:1053-61) reported on the identification and partial characterization of three plasmids from *B. longum* biovar *longum* NAL8 and the construction of an *E. coli*-bifidobacterial shuttle vector, namely pGOSBif33.

Cronin M. et al. (2007, Appl Environ Microbiol. 73:7858-66) described the isolation and sequence of the *Bifidobacterium asteroides* plasmid pCIBA089. Cronin et al. characterized the replication protein and created two *E. coli-Bifidobacterium* shuttle vectors (pPKCm and pSKEM) using the pCIBAO89 replication functions.

Serafini F. et al. (2012, FEMS Microbiol Lett. 333:146-52) reported on the transformation of *B. bifidum* PRL2010 with the broad host range chloramphenicol-resistant plasmid pNZ8048. The procedure involves growth of the strain in a medium with a high concentration (16%) of FOS (fructo-oligosaccharides).

Alvarez-Martin P. et al. (2007, Appl Microbiol Biotechnol. 76:1395-402) described the characterization of the bifidobacterial replication functions on the plasmid pBC1. A set of shuttle vectors were constructed and their use for the genetic accessibility of bifidobacterial strains was evaluated.

Various optimization strategies for genetic transformation of *Bifidobacterium* have been documented. These strategies are based on restriction-modification (R-M) systems, which commonly found in bacteria to provide protection against parasitic invaders such as bacteriophages, and which also allow the cells to discriminate between endogenous (or self) and exogenous DNA. R-M systems appear to be important in *Bifidobacterium*, as R-M gene clusters coding for methyltransferases (MTases) and restriction enzymes (REases), belonging to type I, II and/or IV appear to be present in all sequenced strains of *Bifidobacterium*. The classification of REases is based on their subunit composition, co-factor requirement, recognition sequence structure and the cleavage site relative to the recognition sequence. Type I R-M systems consist of three different subunits, HsdM, HsdR and HsdS that are responsible for modification, restriction and specificity of sequence recognition, respectively. Type I REases require ATP, $Mg^{2+}$ and AdoMet for activity. In general they interact with two asymmetrical bi-partite recognition sites, translocate the DNA in an ATP hydrolysis-dependent manner and cut the DNA distal to the recognition sites, approximately half-way between two sites (Murray N. E., 2002, Microbiology 148:3-20). Typically, in a type II R-M system the REase recognises and usually cleaves within a short (typically between 4 and 8 bp) palindromic DNA sequence. Protection of "self" DNA from restriction occurs by methylation using a MTase, which biochemically modifies specific adenosyl or cytosyl residues within the sequence recognised by the corresponding REase (Kobayashi I., 2001, Nucleic Acids Res. 29:3742-56; Pingoud A. et al., 2005, Cell Mol Life Sci. 62:685-707). Type IV R-M systems are specified by either one of two structural genes encoding an endonuclease with a specificity for methylated, hydroxymethylated or glucosyl-hydroxymethylated bases in the target DNA molecule.

Taken into account the R-M system present in bifidobacteria, a significant increase in transformation efficiency has been reported when *E. coli-Bifidobacterium* shuttle vectors were methylated in *E. coli* by *Bifidobacterium* methylases (see for review Martin P. A. et al., 2010; "Mobile Genetic Elements, Cloning Vectors and Genetic Manipulation of Bifidobacteria" In Bifidobacteria: Genomics and Molecular Aspects; Caister Academic Press; Norfolk, UK; August 2010; Chapter 13; pp 235-259). In particular:

O'Connell Motherway M. et al. (2009, Microb Biotechnol. 2:321-32) have described the identification and characterization of three different R-M systems in *B. breve* UCC2003, including the methylase-specifying genes bbrIM (encoding an isoschizomer of BbeI), bbrIIM (encoding an isoschizomer of SalI) and bbrIIIM (encoding an isoschizomer of PstI). O'Connell Motherway et al. also reported that methylation of plasmid DNA pMAS from *E. coli* by two of these three methylases allows significant improvement of the transformation efficiency of *B. breve* with this plasmid, compared to the un-methylated plasmid.

Kim J. Y. et al. (2010, J Microbiol Biotechnol. 20:1022-6) report that in vitro methylation of plasmid DNA pYBamy59 from *E. coli* by CpG or GpC methyltransferase at SacII sites allows improvement of transformation efficiency of *B. longum* MJ1 with this plasmid, compared to the un-methylated plasmid.

Yasui K. et al. (2008, Nucleic Acids Res. 37:e3) and Suzuki T. et al. (2011, Methods Mol Biol. 765:309-26) describe the methylation of plasmid DNA in *E. coli* by two type II DNA methyltransferases at predicted Sau3AI and KpnII sites, thereby improving transformation efficiency of *B. adolescentis* strains, compared to the un-methylated plasmid. Yasui et al. also describe a system called Plasmid Artificial Modification (PAM), which describes the experimental steps of preparing an appropriate *E. coli* strain containing a PAM vector coding for the methylases of the target host (*Bifidobacterium*), introducing an *E. coli*-*Bifidobacterium* shuttle vector into said *E. coli* strain, modification of the shuttle vector DNA by the methylases coded by the PAM vector, extraction of the methylated shuttle vector DNA and introduction into the *Bifidobacterium* by electroporation.

The above-mentioned methods are based on electroporation for transforming bifidobacteria, but generally these methods still produce a low transformation efficiency and are strain specific.

Dominguez et al. (2013, Microbiology. 159:328-38) developed a conjugation system to transfer genetic material between *E. coli* and *Bifidobacterium* species. Dominguez W. et al. created an *E. coli*-*Bifidobacterium* shuttle vector, namely pDOJHR-WD2, based on plasmid RP4. This vector was transferred from *E. coli* into strains representing four *Bifidobacterium* species, namely *B. bifidum, B. breve, B. longum* subsp. *longum* and *infantis*, and *B. animalis* subsp. *lactis*.

It appears from the foregoing, that there is still a need for molecular tools and improved transformation procedures to allow reliable and efficient transformation of strains of *Bifidobacterium* species.

From the genome analysis of *B. animalis* subsp. *lactis* CNCM I-2494 the inventors have identified that two type II restriction-modification (R-M) systems are encoded by this strain: a first type II R-M system, referred to as BanLI methyltransferase, that encodes a novel methylase and restriction endonuclease, recognizing the nucleotide sequence (A/G)TCAGG and a second type II R-M system that is an isoschizomer of AvaII, referred to as BanLII methyltransferase, recognizing the nucleotide sequence GG(A/T)CC. The inventors have cloned the methylase-encoding genes for each R-M system on the low copy number plasmid pWSK29 (Wang R. F. and Kushner S. R., 1991, Gene, 100:195-199) either singly or together. They have observed that expression of the *B. animalis* subsp. *lactis* CNCM 1-2494 methylases in *E. coli* protects plasmid DNA from restriction with BanLI and BanLII.

Based on the above findings the inventors have developed a transformation procedure and molecular tools to allow efficient transformation of *B. animalis* subsp. *lactis* CNCM I-2494 (which was previously not genetically accessible), thereby making this strain genetically accessible. This transformation procedure and associated molecular tools can be applied to any *Bifidobacterium* species to improve the *Bifidobacterium* transformation efficiency.

Accordingly, the present invention provides a method for genetically transforming a *Bifidobacterium* strain comprising the following steps:

i) transforming an *Escherichia coli* strain or a Gram-positive bacterium strain such as a *Lactobacillus* species or a *Bacillus* species, preferably an *E. coli* strain, either with a recombinant vector DNA comprising a gene encoding a methyltransferase enzyme from a *Bifidobacterium* that methylates the adenine base (i.e., adenosyl residue) at position 4 of the nucleotide sequence RTCAGG (referred to as BanLI methyltransferase) and a recombinant vector DNA comprising a gene encoding a methyltransferase enzyme from a *Bifidobacterium* that methylates the cytosine base (i.e., cytosyl residue) at position 4 of the nucleotide sequence GGWCC (referred to as BanLII methyltransferase), or with a recombinant vector DNA comprising both a gene encoding a BanLI methyltransferase from a *Bifidobacterium* and a gene encoding a BanLII methyltransferase from a *Bifidobacterium*, wherein said recombinant vectors DNA are capable of replicating in said *E. coli* or Gram-positive bacterium strain, ii) transforming the *E. coli* or Gram-positive bacterium strain of step i) with a recombinant shuttle vector DNA comprising a DNA sequence of interest to introduce in a *Bifidobacterium* strain, wherein said shuttle vector DNA is capable of replicating in the *E. coli* or the Gram-positive bacteria strain of step i) and in the *Bifidobacterium* strain to be targeted for genetic transformation, iii) cultivating the transformed *E. coli* or Gram-positive bacterium strain obtained in step ii), iv) extracting the shuttle vector DNA from the transformed *E. coli* or Gram-positive bacterium strain, v) transforming (e.g., electrotransforming) the *Bifidobacterium* strain with the shuttle vector DNA obtained from step iv), vi) recovering the transformed *Bifidobacterium* strain of step v).

In an embodiment of the method according to the invention steps i) and ii) can be carried out in any order or simultaneously.

In another embodiment of the method according to the invention step i) is replaced by a step of providing an *E. coli* or Gram-positive bacterium strain transformed either with a recombinant vector DNA comprising a gene encoding a BanLI methyltransferase from a *Bifidobacterium* and a recombinant vector DNA comprising a gene encoding a BanLII methyltransferase strain from a *Bifidobacterium*, or with a recombinant vector DNA comprising both a gene encoding a BanLI methyltransferase from a *Bifidobacterium* and a gene encoding a BanLII methyltransferase from a *Bifidobacterium*.

In a preferred embodiment of the method according to the invention, the amino acid sequence of the BanLI methyltransferase has at least 60% identity, or by order of increasing preference at least 65%, 70%, 75%, 80%, 85%, 90%, 95%, 96%, 97%, 98%, 99% or 100% identity, with the amino acid sequence SEQ ID NO: 1 (*B. animalis* subsp. *lactis* CNCM 1-2494 Ban LI methyltransferase) and/or the amino acid sequence of the BanLII methyltransferase has at least 55% identity, or by order of increasing preference at least 60%, 65%, 70%, 75%, 80%, 85%, 90%, 95%, 96%, 97%, 98%, 99% or 100% identity, with the amino acid sequence SEQ ID NO: 3 (*B. animalis* subsp. *lactis* CNCM 1-2494 Ban LII methyltransferase).

BanLI methyltransferase (M.BanLI) is a methyltranferase that methylates the internal adenine base of the nucleotide sequence RTCAGG (wherein R represents A or G).

BanLII methyltransferase (M.BanLII) is an isoschizomer of the known AvaII methyltransferase (M.AvaII) from *Anabaena variabilis*, i.e., it methylates the same internal cytosine base of the nucleotide sequence GGWCC (wherein W represents A or T) as M.AvaII.

Advantageously, BanLI methyltransferase and/or BanLII methyltransferase are from a *Bifidobacterium* strain of the same *Bifidobacterium* species as the *Bifidobacterium* strain to be targeted for genetic transformation in step ii). Preferably BanLI methyltransferase and/or BanLII methyltransferase are from the *Bifidobacterium* strain to be targeted for genetic transformation in step ii).

In a preferred embodiment of the method according to the invention BanLI methyltransferase and BanLII methyltransferase are from a *B. animalis* strain, preferably a *B. animalis* subsp *lactis* strain, more preferably from *B. animalis* subsp. *lactis* CNCM 1-2494 (respectively SEQ ID NO: 1 and 3).

Methods for preparing a recombinant DNA vector comprising a gene encoding a methyltransferase enzyme and capable of replicating in an *E. coli* or Gram-positive bacterium strain are well known in the art. These recombinant DNA vectors generally comprise an antibiotic resistance gene, such as an ampicillin or streptomycin resistance gene, a cloning site a replication origin from an *E. coli* (e.g., ColEI ori) and/or a Gram-positive bacterial plasmid and the gene encoding the methyltransferase enzyme, including appropriate sequences to allow expression of the methyltransferase.

Methods for preparing a recombinant shuttle vector DNA comprising a DNA sequence of interest to introduce in a *Bifidobacterium* strain, and capable of replicating both in an *E. coli* or a Gram-positive bacteria strain and in a *Bifidobacterium* strain are known in the art (see e.g., Cronin et al., 2007; Alvarez-Martin et al., 2007; O'Connell Motherway et al., 2009; Kim et al., 2010 and Yasui et al., 2008 all cited above; Patent Application EP 1 829 963). These recombinant shuttle vectors generally comprise an antibiotic resistance gene, such as a tetracycline or chloramphenicol resistance gene, a cloning site and two replication origins including a replication origin from *E. coli* (e.g., ColEI ori) or from a Gram-positive bacterium strain and a replication origin from a *Bifidobacterium* strain (e.g., repB from *B. longum*).

The DNA sequence of interest to introduce in a *Bifidobacterium* strain may, for example, encode proteins that have immuno modulator or anti-tumor properties.

Methods for preparing *E. coli*, Gram positive bacteria and *Bifidobacterium* cells for transformation and methods for transforming these cells are well known in the art. Genetic transformation methods include electroporation (i.e., electrotransformation), transduction, heat shock and protoplast fusion, preferably electroporation.

For genetic transformation protocols of bifidobacteria see for review Martin P. A. et al., 2010; "Mobile Genetic Elements, Cloning Vectors and Genetic Manipulation of Bifidobacteria" In Bifidobacteria: Genomics and Molecular Aspects; Caister Academic Press; Norfolk, UK; August 2010; Chapter 13; pp 235-259.

In an advantageous embodiment of step v), the *Bifidobacterium* strain is cultivated prior to transformation (e.g., electroporation) and/or resuspended after the transformation in an appropriate medium at a temperature comprised between 36° C. and 43° C., preferably between 41° C. and 43° C., more preferably at 42° C.

Said appropriate medium is advantageously a MRS (Man, Rogosa and Sharpes) medium optionally supplemented with cysteine and/or a carbohydrate.

Said appropriate medium is preferably a MRS medium supplemented with cysteine and a carbohydrate.

The carbohydrate can be a xylo-oligosaccharide, lactose, raffinose, stachyose or maltose, preferably maltose.

Advantageously, said MRS medium is a modified MRS medium comprising or consisting of peptone from casein, meat extract, yeast extract, dipotassium hydrogen phosphate ($K_2HPO_4$), potassium dihydrogen phosphate ($KH_2PO_4$), pyruvic acid, polysorbate 80, tri-ammonium citrate, magnesium sulfate hydrate ($MgSO_4.7H_2O$), manganese sulfate hydrate ($MnSO_4.4H_2O$), cysteine-HCl and ferrous sulfate hydrate ($FeSO_4.7H_2O$), that is supplemented with cysteine and maltose.

In a particular embodiment, the modified MRS medium is the medium described in Table 2 below, supplemented with 0.05% cysteine and 1% maltose.

Advantageously, the *Bifidobacterium* strain is cultivated and/or resuspended in the appropriate medium anaerobically.

The present invention also provides a method for genetically transforming a *Bifidobacterium* cell comprising the steps of cultivating the *Bifidobacterium* cell in a first appropriate medium, preparing the competent *Bifidobacterium* cells for transformation, transforming the competent *Bifidobacterium* cells and resuspending the *Bifidobacterium* cells in a second appropriate medium, wherein the first appropriate medium and/or the second appropriate medium is a MRS medium supplemented with cysteine and maltose.

The transformation method includes electroporation, transduction, heat shock and protoplast fusion, preferably electroporation.

In a preferred embodiment, the method for genetically transforming a *Bifidobacterium* cell comprises the steps of cultivating the *Bifidobacterium* cell in a first appropriate medium, preparing the electrocompetent cell, electrotransforming the electrocompetent *Bifidobacterium* cell and resuspending the *Bifidobacterium* cell in a second appropriate medium, wherein the first appropriate medium and/or the second appropriate medium is a MRS medium supplemented with cysteine and maltose.

Advantageously, the MRS medium is a modified MRS medium as defined above.

Advantageously, the *Bifidobacterium* strain is cultivated and/or resuspended in the appropriate medium anaerobically.

Advantageously, the *Bifidobacterium* strain is cultivated and/or resuspended in the appropriate medium at a temperature comprised between 36° C. and 46° C., preferably between 41° C. and 43° C., more preferably at 42° C.

In a particular embodiment, the method for genetically transforming a *Bifidobacterium* cell comprises the steps of:

a) growing a *Bifidobacterium* culture overnight anaerobically at a temperature comprised between 36° C. and 46° C., preferably between 41° C. and 43° C., more preferably at 42° C., in a MRS medium supplemented with cysteine (preferably 0.05% cysteine) and maltose (preferably 1.0% maltose), b) inoculating a fresh modified Rogosa medium supplemented with cysteine (preferably 0.05% cysteine) and maltose (preferably 1.0% cysteine) with the *Bifidobacterium* cells cultured overnight of step a) (advantageously, 4% inoculum).

c) incubating the *Bifidobacterium* cells anaerobically at 36° C. to 46° C., preferably 41° C. to 43° C., more preferably at 42° C., until O.D600 nm reaches ~0.6-0.7, d) harvesting the *Bifidobacterium* cells by centrifugation, advantageously cold rotor at about 4° C., at 6,500 g for 10 mins, e) washing the *Bifidobacterium* cells, advantageously washing twice with ice cold 0.5M sucrose in 1 mM citrate buffer (pH 5.8), f) resuspending the *Bifidobacterium* cells, advantageously resuspending in ice cold buffer, g) electrotransforming the *Bifidobacterium* cells, h) resuspending the *Bifidobacterium* cells in an appropriate medium, preferably a modified Rogosa medium supplemented with cysteine (preferably 0.05% cysteine) and maltose (preferably 1.0% maltose), and incubating the *Bifidobacterium* cells at a temperature comprised between 36° C. and 46° C., preferably between 41° C. and 43° C., more preferably at 42° C.; advantageously incubating for 2 to 6 hours, preferably for 2 to 3 hours, more preferably for 2.5 hours, anaerobically, i) spread plating, preferably aseptically spread plating, serial dilutions of the transformed *Bifidobacterium* cells on Reinforced Clostridial Agar (RCA) medium supplemented with 1% maltose and the appropriate antibiotic, preferably spectinomycin, j) incubation of plates anaerobically at a temperature comprised between 36° C. and 46° C., preferably 42° C., advantageously for 2 to 5 days, preferably for 2.5 days.

Said modified Rogosa medium can be the medium described in Table 2 below.

The *Bifidobacterium* strain transformed according to the methods of the invention can be any strain of the genus *Bifidobacterium*, such as a strain of the species *B. adolescentis*, *B. animalis*, *B. bifidum*, *B. breve*, *B. dentium*, *B. infantis*, *B. longum*, *B. pseudolongum* or *B. thermophilum*.

Preferably, the *Bifidobacterium* strain is a *B. animalis* strain more preferably a *B. animalis* subsp. *lactis* strain and the most preferably the strain *B. animalis* subsp. *lactis* CNCM 1-2494.

The present invention also provides a modified MRS medium comprising or consisting of peptone from casein, meat extract, yeast extract, dipotassium hydrogen phosphate ($K_2HPO_4$), potassium dihydrogen phosphate ($KH_2PO_4$), pyruvic acid, polysorbate 80, tri-ammonium citrate, magnesium sulfate hydrate ($MgSO_4.7H_2O$), manganese sulfate hydrate ($MnSO_4.4H_2O$), cysteine-HCl, ferrous sulfate hydrate ($FeSO_4.7H_2O$), cysteine and maltose.

In a particular embodiment, the modified MRS medium is the medium described in Table 2 below, that is supplemented with 0.05% cysteine and 1% maltose.

The present invention also provides the use of a modified MRS medium according to the present invention for cultivating a bacterium, preferably a *Bifidobacterium* strain (e.g., a strain of the species *B. adolescentis*, *B. animalis*, *B. bifidum*, *B. breve*, *B. infantis*, *B. longum*, *B. pseudolongum* or *B. thermophilum*), more preferably a *B. animalis* strain, and most preferably a *B. animalis* subsp *lactis* strain, such as the strain *B. animalis* subsp. *lactis* CNCM 1-2494.

The present invention also provides an isolated recombinant expression cassette, comprising a polynucleotide sequence encoding an BanLI methyltransferase having at least 60% identity, or by order of increasing preference at least 65%, 70%, 75%, 80%, 85%, 90%, 95%, 96%, 97%, 98%, 99% or 100% identity, with the amino acid sequence SEQ ID NO: 1 (M.BanLI) and/or a polynucleotide sequence encoding a BanLII methyltransferase having at least 55% identity, or by order of increasing preference at least 60%, 65%, 70%, 75%, 80%, 85%, 90%, 95%, 96%, 97%, 98%, 99% or 100% identity with the amino acid sequence SEQ ID NO: 3 (M.BanLII), under control of a promoter functional in a bacterium.

The present invention also provides a recombinant vector comprising a recombinant expression cassette according to the present invention.

The present invention also provides a transformed *Escherichia coli* or Gram-positive bacterium strain, preferably a transformed *E. coli* strain, containing a recombinant vector according to the present invention.

The present invention also provides an isolated cDNA encoding the BanLI methyltransferase, having the nucleotide sequence SEQ ID NO: 2.

The present invention also provides an isolated cDNA encoding the BanLII methyltransferase, having the nucleotide sequence SEQ ID NO: 4.

The present invention also provides an isolated methyltransferase (BanLI) having the amino acid sequence SEQ ID NO: 1.

The present invention also provides an isolated methyltransferase (BanLII) having the amino acid sequence SEQ ID NO: 3.

In addition to the preceding features, the invention further comprises other features which will emerge from the following description, which refers to examples illustrating the present invention, as well as to the appended figures.

Figure 7:
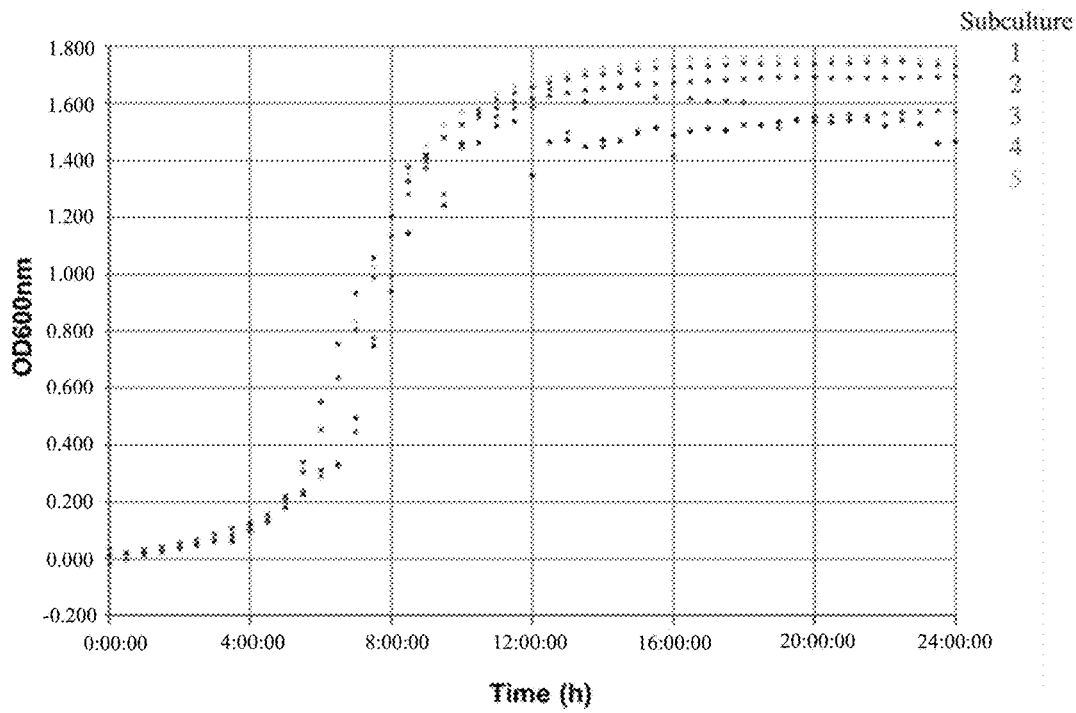

FIG. 7 represents the culture of *B. animalis* subsp. *lactis* CNCM 1-2494 in DM-MRS medium supplemented with 1% maltose and 0.05% cysteine. This medium allows reproducible growth of the strain over 5 consecutive subcultures.

Figure 8:
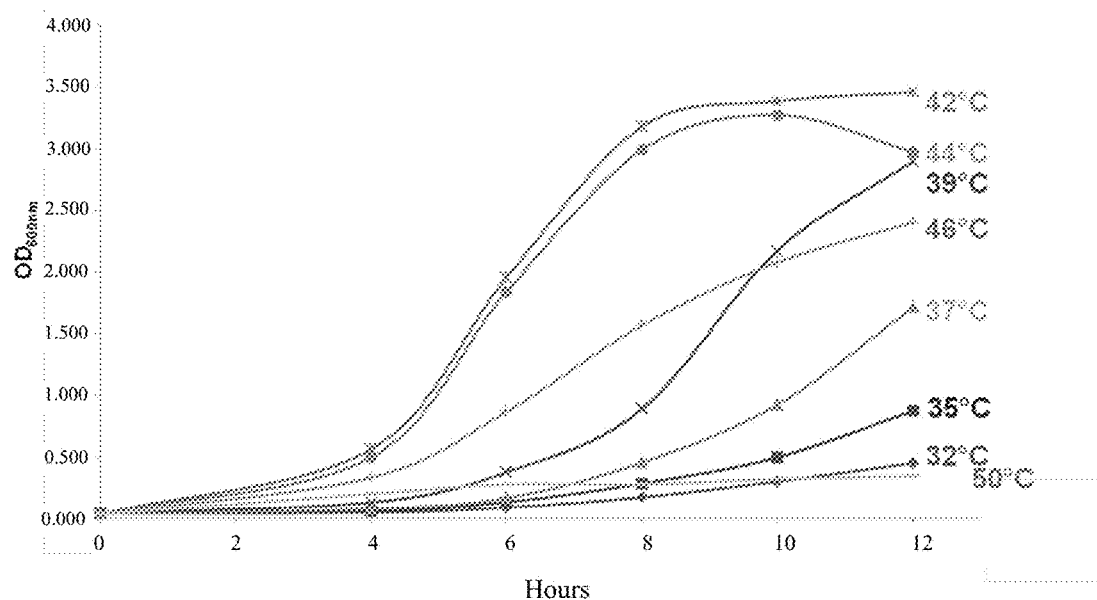

FIG. 8 represents the growth profiles of *B. animalis* subsp. *lactis* CNCM 1-2494 at temperatures ranging from 32° C. to 50° C. in DM-MRS medium supplemented with 1% maltose and 0.05% cysteine.

EXAMPLE 1

Genetic Transformation of *Bifidobacterium Animalis* Subsp. *Lactis* CNCM I-2494

Materials and Methods

Cloning of Genes Encoding Methyltransferases M.BanLI and M.BanLII

Figure 1:
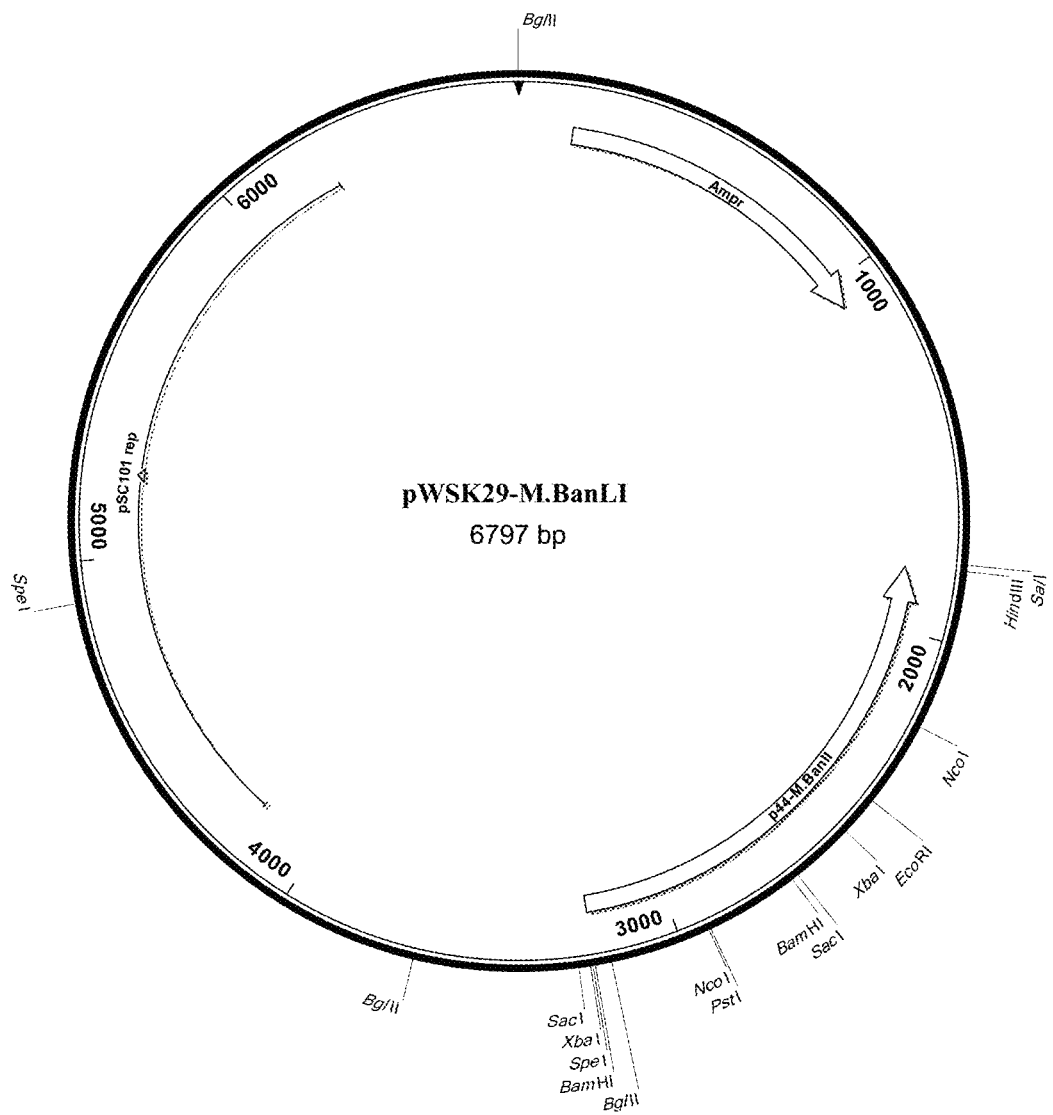
FIG. 1 represents the plasmid map of expression vector pWSK29-M.BanLI.
Figure 2:
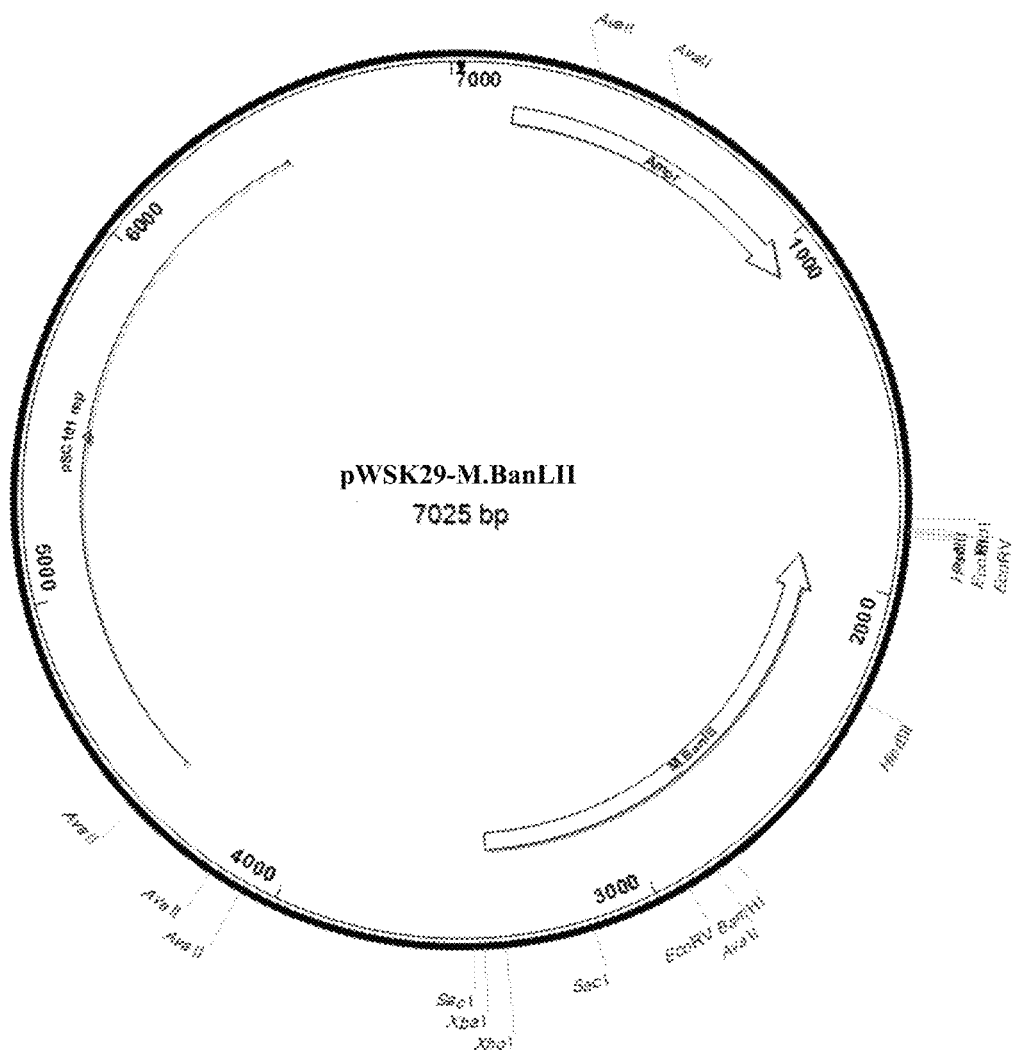
FIG. 2 represents the plasmid map of expression vector pWSK29-M.BanLII.

For the construction of plasmids pWSK29-M.BanLI (see FIG. 1) and pWSK29-M.BanLII (see FIG. 2), DNA fragments encompassing the coding sequences of BanLI methyltransferase and BanLII methyltransferase were generated by PCR amplification from chromosomal DNA of *B. animalis* subsp. *lactis* CNCM 1-2494 using PFU Ultra DNA polymerase and primer combinations BanLIF and BanLIR or BanLIIF and BanLIIR (see Table 1 below).

TABLE 1

Oligonucleotide primers used in this Example

| Purpose | Primer | Sequence | SEQ ID NO: |
|---|---|---|---|
| Cloning of m.BanLI in pNZ44 | BanLIF | cgtccgctgcagataagga ggcactcaccatggctacg cctctcaatcgag | 5 |
| | BanLIR | gctctataagcttttactt tccttgcgcttcttc | 6 |
| Cloning of p44-MBanLI in pWSK29 | BanLIF1 | cgtccgagatctgttagtt gaagaaggttttatatta cag | 7 |
| Construction of transcriptional fusion of BanLII to plac on pWSK29 | BanLIIF | cgtccgtctagaataagga ggcactcaccatgccgcgt gtgttcaattg | 8 |
| | BanLIIR | gctctactgcagcaatgga ggcgtgcaaatc | 9 |
| Construction of pWSK29-M.BanLI-M.BanLII | BanLIF2 | tcagctgtcgacacaattg taacccatacaggag | 10 |
| | BanLIR2 | gcgacggtcgactttactt tccttgcgcttcttc | 11 |
| Construction of pDM1 | SpecF | gtcctggagctcgcacacg aaaaacaagttaag | 12 |
| | SpecR | ctggaagagctccaatgaat aggtttacacttactttag | 13 |
| Construction of pDM2 | SpecF1 | ctggaaaagcttcaatgaat aggtttacacttactttag | 14 |
| | SpecR1 | gtcctggaattcgcacacga aaaacaagttaag | 15 |

Each forward primer contained the sequence of a ribosome binding site to facilitate translation of each mRNA. For the BanLI-encoding fragment PstI and HindIII sites were incorporated into the forward and reverse primers, respectively to facilitate ligation to similarly digested pNZ44 (McGrath S. et al., 2001, Appl Environ Microbiol. 67:608-616). Ligations were electroporated into *L. lactis* NZ9000 (Kuipers O. P. et al., 1993, Eur J Biochem. 216: 281-291; Kuipers O. P. et al., 1998, J Biotechnol. 64:15-21) and transformants selected based on chloramphenicol resistance. The presence and integrity of the cloned insert was confirmed by restriction analysis followed by sequencing of the BanLI insert. The BanLI-encoding sequence, together with the constitutive p44 lactococcal promoter, specified by pNZ44, were amplified by PCR from a representative pNZ44-BanLI plasmid using the primer pair BanLIF1 and BanLIR (see Table 1). The resultant fragment was restricted with BglII and HindIII and ligated to the compatible BamHI and HindIII sites on pWSK29 (Wang R. F. and Kushner S. R., 1991, Gene, 100:195-199). For the construction of pWSK29-M.BanLII (M.AvaII) the M.BanLII-encoding sequence was transcriptionally fused to the lac promoter on pWSK29. The amplified fragment was restricted with XbaI and PstI and ligated to similarly digested pWSK29. Each ligation was transformed into *E. coli* X11Blue. The plasmid content of a number of Amp$^r$ transformants was screened by restriction analysis and the integrity of positively identified clones was verified by sequencing. The resultant plasmids were designated pWSK29-M.BanLI and pWSK29-M.BanLII.

Figure 3:
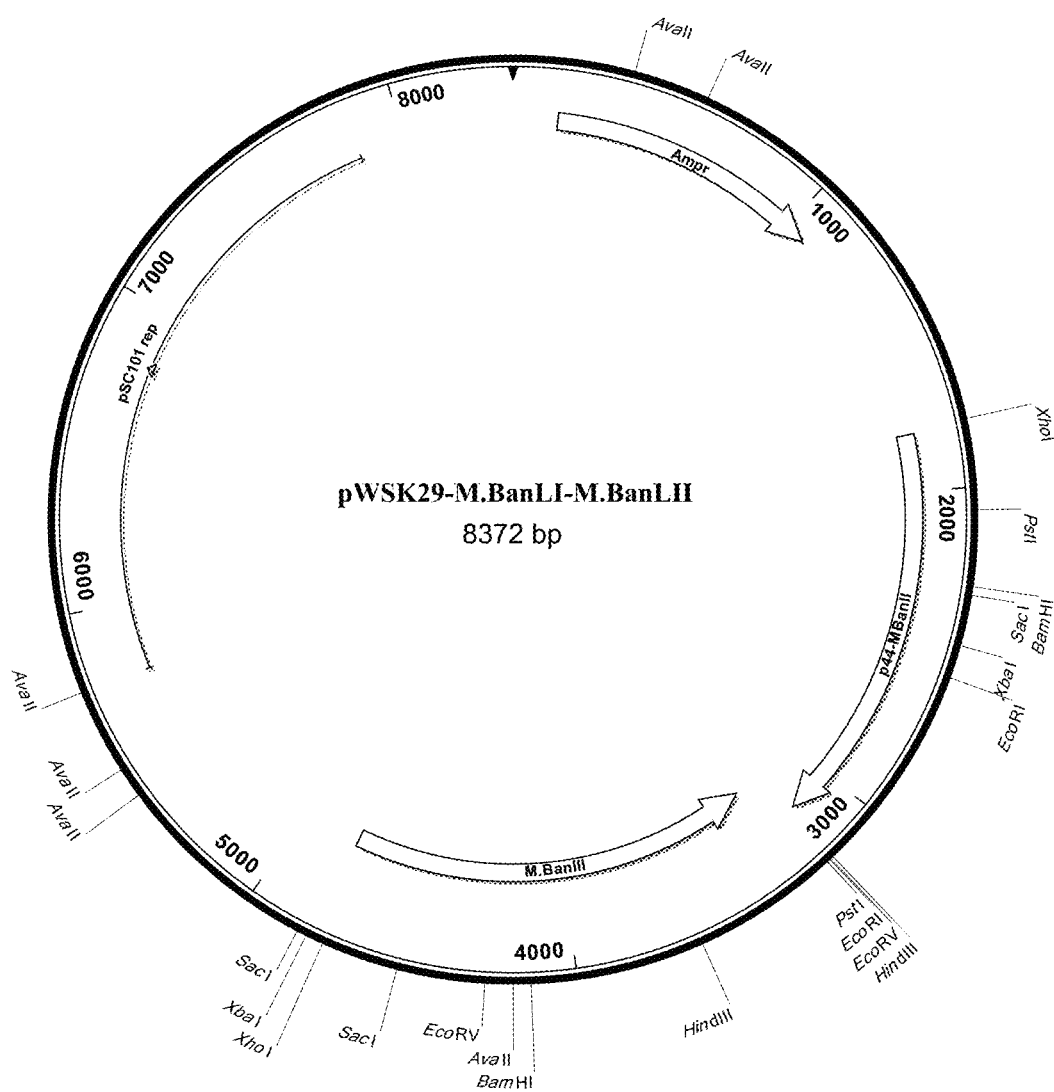
FIG. 3 represents the plasmid map of expression vector pWSK29-M.BanLI-M.BanLII.
Figure 4:
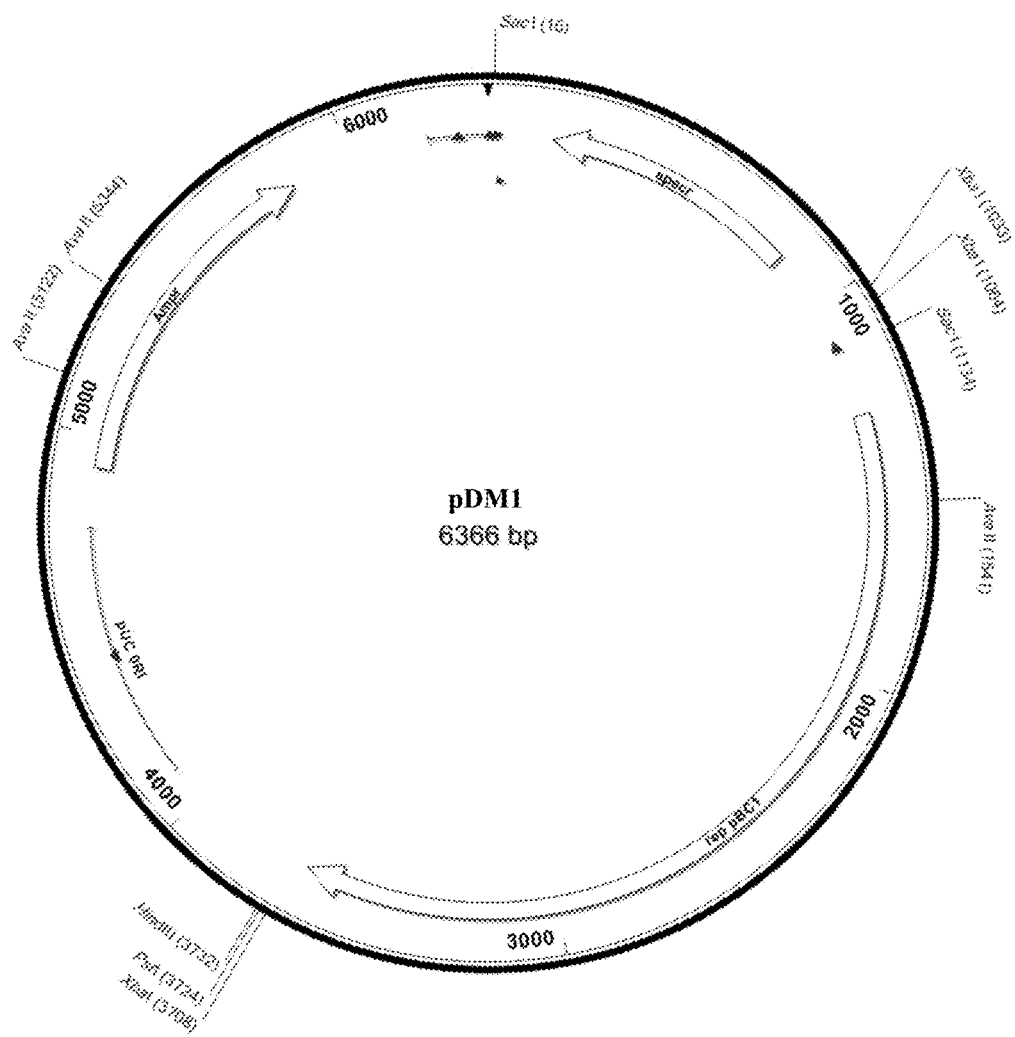
FIG. 4 represents the plasmid map of the replicative vector pDM1.
Figure 5:
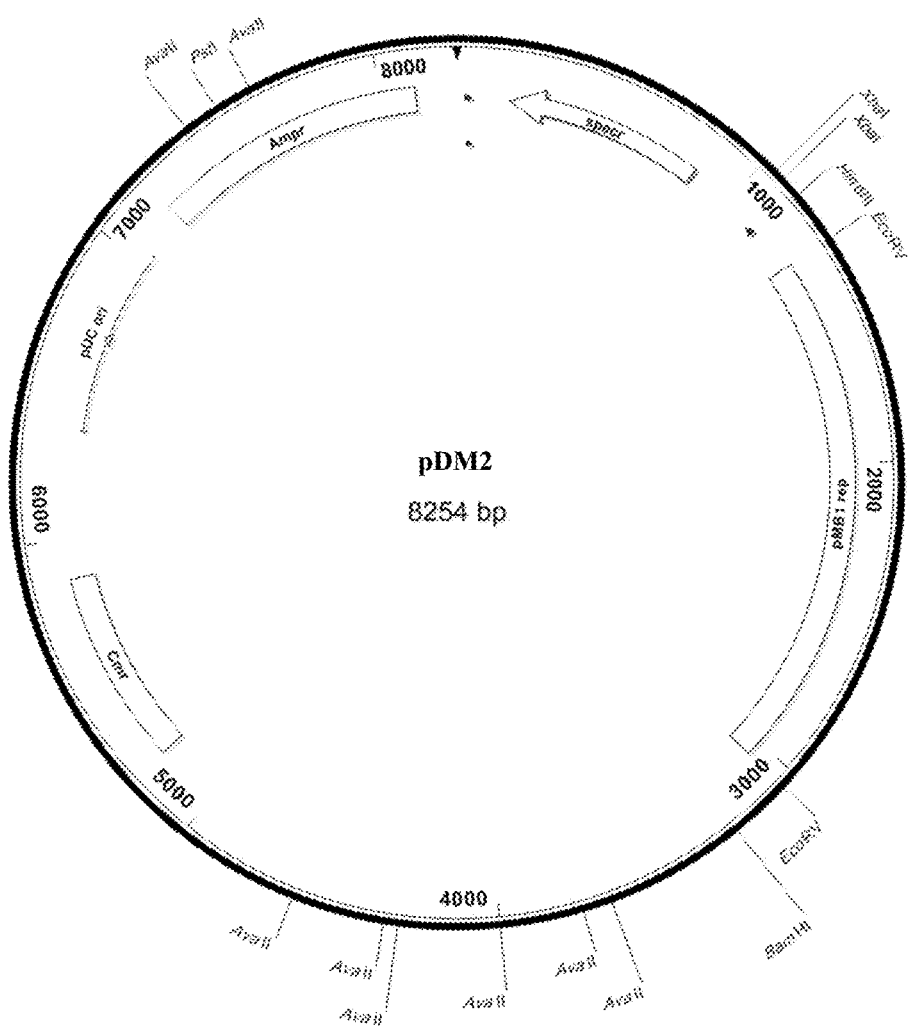
FIG. 5 represents the plasmid map of the replicative vector pDM2.

For plasmid pWSK29-M.BanLI-M.BanLII (see FIG. 3), which expresses two of the identified *B. animalis* subsp. *lactis* CNCM 1-2494 methyltransferases, the DNA fragment encompassing p44-M.BanLI was amplified from pWSK29-M.BanLI by PCR using primer combinations BanLIF2 and BanLIR2 (see Table 1), both of which had SalI restriction sites incorporated at their 5' ends. The resulting amplicon was digested with SalI, and ligated into similarly digested pWSK29-M.BanLII. The resulting ligation mixture was introduced into *E. coli* X11Blue by electrotransformation and transformants selected based on ampicillin resistance. The plasmid content of a number of Amp$^r$ transformants was screened by restriction analysis and the integrity of positively identified clones was verified by sequencing.

Construction of the Replicative Plasmids pDM1 (pAMS-spec) and pDM2 (pDG7-spec)

The spectinomycin resistance gene together with its own promoter were amplified from pMG36 (van de Guchte M. et al., 1989, Appl Environ Microbiol. 55:224-8) carrying a spectinomycin resistant marker (pMG36S), using the primer combinations SpecF and SpecR (see Table 1) that harbor SacI sites at their 5' end or SpecF1 and SpecR1 (see Table 1) that contain EcoRI and HindIII sites, respectively. In each case the 1117 bp amplicon was digested with either SacI or a combination of EcoRI and HinDIII and ligated to similarly digested pAMS (Alvarez-Martin et al., 2007, cited above) or pDG7 (Argnani et al., 1996, cited above), respectively. The ligations were transformed into *E. coli* EC101 with selection on LB agar containing spectinomycin. A number of spectinomycin-resistant transformants were selected and screened for plasmid content by restriction analysis and DNA sequencing. In the resultant plasmid, pDM1, the tet$^r$ cassette of pAMS was replaced with the spectinomycin resistance cassette, while pDM2 is pDG7 harbouring the spectinomycin cassette cloned in the unique EcoRI and HinDIII sites.

Transformation of *B. animalis* subsp. *lactis* CNCM I-2494

48 ml of DM-MRS (see Table 2 below) supplemented with 0.05% cysteine and 1% maltose was inoculated with 2 ml of an overnight culture of *B. animalis* subsp. *lactis* CNCM 1-2494 and incubated anaerobically at 42° C. (DM-MRS is autoclaved at 121° C. for 15 min. Prior to inoculation DM-MRS is supplemented with cysteine HCL 0.05% and maltose 1%.

TABLE 2

Composition of DM-MRS broth

| | g/L |
|---|---|
| Difco Proteose Peptone No. 3 | 10 g |
| Difco Beef Extract | 10 g |
| Difco Yeast Extract | 5 g |
| Polysorbate (Tween) 80 | 1 ml |
| Tri-ammonium citrate | 2 g |
| $MgSO_4 \cdot 7H_2O$ | 0.575 g |
| $MnSO_4 \cdot 4H_2O$ | 0.120 g |
| $K_2HPO_4$ | 3 g |
| $KH_2PO_4$ | 3 g |
| Pyruvic acid | 0.2 g |
| Cysteine-HCl | 0.3 g |
| $FeSO_4 \cdot 7H_2O$ | 0.034 g | pH 6.8

At an optical density (OD600 nm) of approximately 0.8, the bacterial cells were collected by centrifugation at 6,500 g for 10 min at 4° C., and the pellet washed twice with chilled sucrose citrate buffer (1 mM citrate [pH 5.8], 0.5 M sucrose). The cells were subsequently suspended in 300 μl of chilled sucrose citrate buffer. Fifty microliters of the cell suspension was used for each electrotransformation, the cells and plasmid DNA were mixed and held on ice prior to the pulse at 25 μF, 200 ohms and 2 kV. After transformation, the cells were suspended in 1 ml of DM-MRS supplemented with cysteine and maltose and incubated for 3 hours at 42° C. Serial dilutions were plated on RCA supplemented with maltose and containing the appropriate antibiotic and incubated at 42° C. for 24-36 h at which point transformant colonies were visible.

Results

Figure 6:
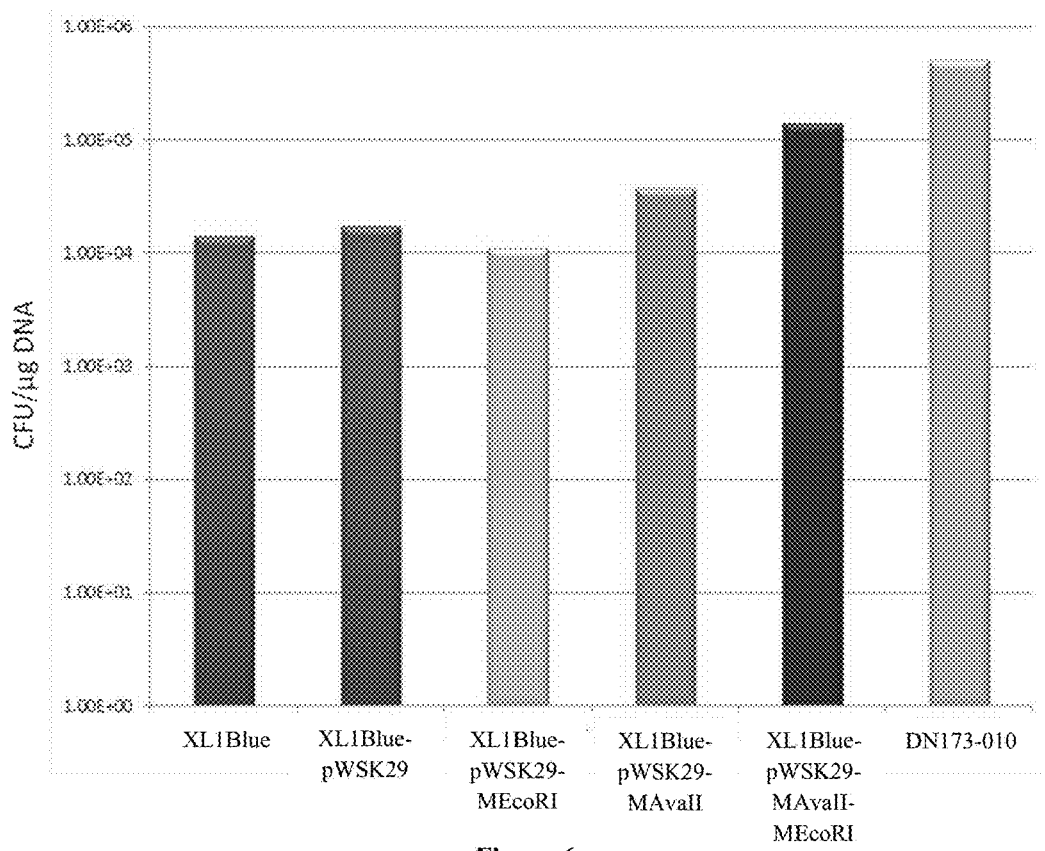
FIG. 6 represents the transformation efficiencies of *B. animalis* subsp. *lactis* CNCM 1-2494 with pDM1 isolated from *E. coli* (XL1Blue), XL1Blue harbouring pWSK29, or derivatives harbouring the individual methylase encoding genes singly or in combination. The final column represents the transformation efficiency of pDM1 isolated from *B. animalis* subsp. *lactis* CNCM I-2494 (DN 173-010).

The results (see FIG. 6) show that the transformation efficiency of *B. animalis* subsp *lactis* CNCM 1-2494 with pDM1 DNA isolated from genetically modified *E. coli* habouring BanLI and BanLII methyltransferase encoding genes increases by 10 fold as compared to un-methylated pDM1 DNA.

EXAMPLE 2

Development of a Growth Medium for Growing *A Bifidobacterium* Strain

Following testing of various growth media, a modified MRS medium (named DM-MRS; see Table 2 above) was formulated. This medium allows *B. animalis* subsp. *lactis* CNCM I-2494 be reproducibly subcultured in the presence of 1% maltose and 0.05% cysteine over five consecutive subcultures (FIG. 7). This medium further allows growth that is entirely dependent on the supplementation of maltose as the sole carbon and energy source of the strain.

Further, the temperature of 42° C. is an optimum temperature for growing *B. animalis* subsp. *lactis* CNCM 1-2494 in DM-MRS (see FIG. 8).

---

The invention claimed is:

1. A method for genetically transforming a *Bifidobacterium* strain, the method comprising:

transforming an *Escherichia coli* strain or a Gram-positive bacterium strain either with a recombinant vector DNA comprising a gene encoding a methyltransferase enzyme from a *Bifidobacterium* that methylates the adenine base at position 4 of the nucleotide sequence RTCAGG (BanLI methyltransferase) and a recombinant vector DNA comprising a gene encoding a methyltransferase enzyme from a *Bifidobacterium* that methylates the cytosine base at position 4 of the nucleotide sequence GGWCC (BanLII methyltransferase), or with a recombinant vector DNA comprising both a gene encoding a BanLI methyltransferase from a *Bifidobacterium* and a gene encoding a BanLII methyltransferase from a *Bifidobacterium*, wherein said recombinant vectors DNA are capable of replicating in said *E. coli* or Gram-positive bacterium strain, ii) transforming the *E. coli* or Gram-positive bacterium strain obtained after step i) with a recombinant shuttle vector DNA comprising a DNA sequence of interest to introduce in a *Bifidobacterium* strain, wherein the said shuttle vector DNA is capable of replicating in the *E. coli* or the Gram-positive bacteria strain of step i) and in the *Bifidobacterium* strain to be targeted for genetic transformation, iii) cultivating the transformed *E. coli* or Gram-positive bacterium strain obtained in step ii), iv) extracting the shuttle vector DNA from the transformed *E. coli* or Gram-positive bacterium strain, v) transforming, preferably electrotransforming, a *Bifidobacterium* strain with the shuttle vector DNA obtained from step iv), vi) recovering the transformed *Bifidobacterium* strain of step v).

2. The method according to claim 1, wherein step i) is replaced by a step of providing an *E. coli* or Gram-positive bacterium strain transformed either with a recombinant vector DNA comprising a gene encoding a BanLI methyltransferase from a *Bifidobacterium* and a recombinant vector DNA comprising a gene encoding a BanLII methyltransferase strain from a *Bifidobacterium*, or with a recombinant vector DNA comprising both a gene encoding a BanLI methyltransferase from a *Bifidobacterium* and a gene encoding a BanLII methyltransferase from a *Bifidobacterium*.

3. The method according claim 1, wherein the amino acid sequence of the BanLI methyltransferase has at least 60% identity with the amino acid sequence SEQ ID NO: 1 and/or the amino acid sequence of the BanLII methyltransferase has at least 55% identity with the amino acid sequence SEQ ID NO:3.

4. The method according to claim 1, wherein the BanLI methyltransferase or the BanLII methyltransferase are from a *Bifidobacterium* strain of the same *Bifidobacterium* species as the *Bifidobacterium* strain to be targeted for genetic transformation in step ii).

5. The method according claim 1, wherein the *Bifidobacterium* strain is cultivated prior to transformation and/or resuspended after the transformation in an appropriate medium at a temperature between 36° C. and 46° C., preferably between 41° C. and 43° C., more preferably at 42° C.

6. The method according to claim 5, wherein the said appropriate medium is a Man, Rogosa and Sharpes medium supplemented with cysteine and a carbohydrate (DM-MRS).

7. The method according to claim 1, wherein each of the transformation steps is carried out by a method selected from the group consisting of electroporation, transduction, heat shock, and protoplast fusion.

8. The method according to claim 1, wherein the *Bifidobacterium* strain is selected from the group consisting of a strain of the species *B. adolescentis, B. animalis, B. bifidum, B. breve, B. dentium, B. infantis, B. longum, B. pseudolongum* and *B. thermophilum*, preferably a strain of the species *B. animalis*.

9. A transformed *Escherichia coli* or Gram-positive bacterium strain, comprising a recombinant vector, wherein the vector comprises a recombinant cassette comprising a polynucleotide sequence encoding a BanLI methyltransferase having at least 60% identity with the amino acid sequence SEQ ID NO: 1 and/or a polynucleotide sequence encoding a BanLII methyltransferase having at least 55% identity with the amino acid sequence SEQ ID NO: 3, under control of a promoter that is functional in the bacterium.

* * * * *